US012290545B2

(12) United States Patent
Planckaert

(10) Patent No.: US 12,290,545 B2
(45) Date of Patent: May 6, 2025

(54) **COMPOSITION COMPRISING CHICORY ROOT AND PEA CELL WALL FIBER FOR TREATING *BRACHYSPIRA* INFECTIONS**

(71) Applicant: Cosucra Groupe Warcoing S.A., Warcoing (BE)

(72) Inventor: Philippe Planckaert, Rollegem (BE)

(73) Assignee: Cosucra Groupe Warcoing S.A., Warcoing (BE)

( * ) Notice: Subject to any disclaimer, the term of this patent is extended or adjusted under 35 U.S.C. 154(b) by 897 days.

(21) Appl. No.: 17/311,379

(22) PCT Filed: Dec. 19, 2019

(86) PCT No.: PCT/EP2019/086157
§ 371 (c)(1),
(2) Date: Jun. 7, 2021

(87) PCT Pub. No.: WO2020/127630
PCT Pub. Date: Jun. 25, 2020

(65) Prior Publication Data
US 2022/0023368 A1    Jan. 27, 2022

(30) Foreign Application Priority Data

Dec. 19, 2018 (EP) .................................. 18213874

(51) Int. Cl.
| | | |
|---|---|---|
| *A61K 36/48* | (2006.01) | |
| *A23K 10/30* | (2016.01) | |
| *A23K 20/163* | (2016.01) | |
| *A23K 50/30* | (2016.01) | |
| *A23K 50/75* | (2016.01) | |
| *A23L 2/52* | (2006.01) | |
| *A23L 33/00* | (2016.01) | |
| *A23L 33/105* | (2016.01) | |
| *A23L 33/125* | (2016.01) | |
| *A23L 33/22* | (2016.01) | |
| *A23L 33/24* | (2016.01) | |
| *A61K 31/343* | (2006.01) | |
| *A61K 31/733* | (2006.01) | |
| *A61K 36/28* | (2006.01) | |
| *A61P 31/04* | (2006.01) | |

(52) U.S. Cl.
CPC .............. *A61K 36/48* (2013.01); *A23K 10/30* (2016.05); *A23K 20/163* (2016.05); *A23K 50/30* (2016.05); *A23K 50/75* (2016.05); *A23L 2/52* (2013.01); *A23L 33/105* (2016.08); *A23L 33/125* (2016.08); *A23L 33/22* (2016.08); *A23L 33/24* (2016.08); *A23L 33/40* (2016.08); *A61K 31/343* (2013.01); *A61K 31/733* (2013.01); *A61K 36/28* (2013.01); *A61P 31/04* (2018.01); *A23V 2002/00* (2013.01)

(58) Field of Classification Search
None
See application file for complete search history.

(56) References Cited

U.S. PATENT DOCUMENTS

| | | |
|---|---|---|
| 6,489,310 B1 | 12/2002 | Brassart et al. |
| 2012/0135957 A1 | 5/2012 | Dugenet et al. |
| 2012/0269865 A1 | 10/2012 | Roughead et al. |
| 2016/0100617 A1 | 4/2016 | Roughead et al. |
| 2016/0263145 A1 | 9/2016 | Dugenet et al. |

FOREIGN PATENT DOCUMENTS

| | | |
|---|---|---|
| EP | 1 010 374 A1 | 6/2000 |
| WO | 2011020853 A1 | 2/2011 |
| WO | 2011060123 A1 | 5/2011 |

OTHER PUBLICATIONS

PCT International Search Report dated Mar. 12, 2020 in connection with PCT/EP2019/086157.
PCT Written Opinion of the International Searching Authority Report dated Mar. 12, 2020 in connection with PCT/EP2019/086157.
Hansen et al: "Diets containing inulin but not lupins help to prevent swine dysentery in experimentally challenged pigs1", Journal of Animal Science, vol. 88, No. 10. Oct. 1, 2010 (Oct. 1, 2010), pp. 3327-3336, XP055632495.
Thomsen et al: "The effect of fermentable carbohydrates on experimental swine dysentery and whip worm infections in pigs", Veterinary Microbiology, Elsevier BV, NL, vol. 119, No. 2-4, Jan. 4, 2007 (Jan. 4, 2007), pp. 162-163, XP005821850.
Chen et al: "Dietary fibre affects intestinal mucosal barrier function and regulates intestinal bacteria in weaning piglets", British Journal of Nutrition, vol. 110, No. 10, May 9, 2013 (May 9, 2013), pp. 1837-1848, XP055632720.
Halas et al: "Effect of dietary supplementation with inulin and/or benzoic acid on the incidence and severity of post-weaning diarrhoea in weaner pigs after experimental challenge with enterotoxigenic *Escherichia coli*", Archives of Animal Nutrition, vol. 63, No. 4, Jul. 29, 2009 (Jan. 29, 2009), pp. 267-280, XP055633042.

*Primary Examiner* — Isis A Ghali
(74) *Attorney, Agent, or Firm* — Amster, Rothstein & Ebenstein LLP

(57) ABSTRACT

The present invention relates to compositions comprising dried chicory root and pea cell wall fibers for reducing, preventing and/or treating dysentery in animals, poultry and humans. The invention also relates to the use of said compositions in feed and food.

16 Claims, No Drawings

COMPOSITION COMPRISING CHICORY ROOT AND PEA CELL WALL FIBER FOR TREATING *BRACHYSPIRA* INFECTIONS

CROSS-REFERENCE TO RELATED APPLICATIONS

This application is a U.S. national stage entry under 35 U.S.C. § 371 of PCT International Patent Application No. PCT/EP2019/086157, filed Dec. 19, 2019, which claims priority to European Patent Application No. 18213874.3, filed Dec. 19, 2018, the contents of each of which are incorporated herein by reference in their entirety.

FIELD OF THE INVENTION

The present invention is situated in the field of animal and human food and feed supplements, more specifically it relates to compositions comprising dried chicory roots and pea cell wall fiber for reducing, treating or preventing dysentery in animals and humans. The present invention also concerns the use of such compositions in farming of livestock and poultry. As such the present invention also concerns the use of a composition comprising chicory fiber and pea fiber for the preparation of a food, a feed or a medicament.

BACKGROUND OF THE INVENTION

Intestinal spirochetes of the genus *Brachyspira* are oxygen-tolerant, anaerobic microorganisms that colonize the colon and cecum of different animal species, whose pathogenic variants can cause swine dysentery and Intestinal Spirochetosis in pigs, humans, dogs, rhesus monkeys, baboons and various other animal species. *B. hyodysenteriae* and *B. pilosicoli* are well-known pathogenic species which cause swine dysentery and Porcine Intestinal Spirochetosis (PIS)/Avian Intestinal Spirochetosis (AIS) respectively (Taylor en Alexander, 1971; Harris et al., 1972; Harris et al., 1972; Taylor et al., 1980; Trott et al., 1996a; Stephens en hampson, 2002a; Stanton et al., 1998; Hampson en McLaren, 1999). In addition to the clinical disease, the disease can also manifest itself sub clinically, resulting in growth retardation and major economic losses. "*B. suanatina*" can induce symptoms that are very similar to the symptoms of swine dysentery (Råsbäck et al., 2007). *B. hampsonii* and β-hemolytic isolates of *B. intermedia* can also induce analogous lesions such as *B. hyodysenteriae* (Burrough et al., 2012).

The elimination of a *B. hyodysenteriae* infection can be achieved in two ways, first by a drastic depopulation or second by treatment of all pigs with antimicrobial agents. In the latter case, either all pigs are treated in combination with strict hygiene and rodent control, or the sows are treated until they are free of infection, after which the piglets are reared separately in a hygienic, germ-free environment. The latter requires very strict operations and is often more difficult to apply.

Pigs from regions with presence of *Brachyspira* are mostly treated preventively with antibiotics, such as Tiamulin. However, Resistance against antimicrobial agents that are active against *Brachyspira* spp. is widespread (Movahedi en Hampson, 2010). Today, the European regulations intend to reduce the use of antibiotics to avoid resistance of bacteria to antibiotics as well for the animals as for human consumers of the meat.

An alternative treatment method against *Brachyspira* spp. is based on a component from the chicory root. Thomson et al. (2007, Veterinary Microbiology, Vol. 119, no. 2-4) assumed that a chicory root and lupine-containing diet will protect pigs against the development of swine dysentery. However, Hansen et al. (2010, J. Animal Science, vol. 88, no. 10) demonstrated that the feeding of 80 g-kg of LG inulin, a fructo-oligosaccharide dietary fiber extracted from chicory roots, protected pigs from dysentery rather than the component lupine.

There is therefore still a need to develop compositions having improved physiological and/or pharmacological and/or therapeutic activities preventing and/or treating *Brachyspira* infection in animals and humans. It is accordingly one of the objects of the present invention to overcome or ameliorate at least one of the disadvantages of the prior art, or to provide a useful alternative.

SUMMARY OF THE INVENTION

The present inventors surprisingly found that a combination of dried chicory root and pea cell wall fibers, i.e. the fibers present in dehulled peas (pea inner cell-wall fibers) and the fibers present in the outer hull (pea outer-cell wall fibers), can counter dysentery in animals, poultry and humans. This seems to be due to the combined effect of inulin and sesquiterpene lactones from the dried chicory root, which are retained longer in the gut of the treated subject due to the effect of the pea cell wall fibers. The present inventors have found that the present composition has a positive and synergistic effect on the treatment of animals with pathogenic *Brachyspira* infection.

Thanks to the synergistic effect of the dried chicory root component and the pea cell wall fibers in the present composition, the quantity of inulin from the dried chicory root needed to be used to effectively treat animals with pathogenic *Brachyspira* infection is much lower compare to the prior art compositions.

Therefore, the present invention concerns a composition comprising a dried chicory root component and a pea cell wall fiber component, for reducing, treating or preventing of *Brachyspira* infection in animals, poultry and humans. Preferably the pea cell wall fiber and dried chicory root component in said composition are present within a weight ratio of between 1/2 and 2/1, such as between 1/1.5 and 1.5/1, such as about 1/1.

There are many plant fibres (carrots, wheat, soya, bamboo, etc.), but pea fibres have a unique combination of physicochemical characteristics, for example a high water retention, an excellent oil retention and excellent gel strength for applications in products intended for food for human consumption or animal feed (cf. WO2016180888 (A1)). Indeed, the pea fibres is highly functional and profitable. It helps to reduce losses upon cooking and to improve the yields of various meat-based preparations. The invention provides for the following aspects:

Aspect 1. A composition comprising dried chicory root and pea cell wall fibers (pea fiber from dehulled peas) for use in reducing, treating or preventing infections with pathogenic *Brachyspira* ssp. in animals, poultry and humans and wherein said composition is administered in an amount of between 0.1 to 10% by weight, more preferably in an amount of between 0.1 to 5% by weight of the total dry matter feed of the animal or poultry.

Aspect 2. The composition according to claim 1, wherein the weight ratio of said dried chicory root to said pea cell wall fiber is between 1/2 and 2/1, preferably between 1:1.5 and 1.5/1, more preferably wherein said weight ratio is about 1/1.

Aspect 3. The composition according to claim 1 or 2, wherein said dried chicory root comprises inulin, sesquiterpene lactones, a soluble fraction and an insoluble fraction, preferably wherein said insoluble fraction comprises pulp and/or the soluble fraction comprises pectin.

Aspect 4. The composition according to any one of claims 1 to 3, wherein said dried chicory root comprises at least 50% by weight of inulin, preferably at least 60% by weight of inulin, typically of about 65% by weight, and/or comprises between 0.3 and 0.5% by weight such as about 0.4% by weight of sesquiterpene lactones. Said inulin typically has an average degree of polymerization by number of at least 3.

Aspect 5. The composition according to any one of claims 1 to 4 wherein said dried chicory root comprises sesquiterpene lactones chosen from the group consisting of: lactucin, dihydrolactucin, lactucopicrin and dihydrolactucopicrin.

Aspect 6. The composition for use according to any one of claims 1 to 5, wherein said pea cell wall fiber is pea fibre from dehulled peas (pea inner cell-wall fibers), or said pea cell wall fiber is pea fiber present in the outer hull (pea outer-cell wall fibers), more preferably of yellow pea or green pea.

Aspect 7. The composition for use according to any one of claims 1 to 6, wherein said pea cell wall fiber component comprises about 50% by weight fibers and about 48% by weight starch.

Aspect 8. The composition for use according to any one of claims 1 to 7, wherein the fiber component of said pea cell wall fiber comprises about 15% by weight cellulose, about 40% by weight pectin and about 45% by weight hemicellulose.

Aspect 9. The composition for use according to any one of claims 1 to 8, wherein said pathogenic *Brachyspira* infection is resulting in a disorder selected from: swine dysentery, Porcine Intestinal Spirochetosis (PIS), Avian Intestinal Spirochetosis (AIS), and Human Intestinal Spirochetosis (HIS).

Aspect 10. The composition for use according to any one of claims 1 to 9 wherein said pathogenic *Brachyspira* infection is caused by any one or more of: *B. murdochii B. innocens B. intermedia B. hyodysenteriae, B. pilosicoli, B. suanatina, B. hampsonii, B. canis* and *B. aalborgi*.

Aspect 11. The composition for use according to any one of claims 1 to 10, wherein said pea cell wall fiber and dried chicory root components are administered simultaneously or wherein said pea cell wall fiber component is administered prior to administration of the dried chicory root composition. The inclusion of pea cell wall fiber is specifically intended to work as a carrier in order to stop the diarrheic liquid faeces on very short term. Once the faeces are under control, pea cell wall fiber could be withdrawn from the formula, although it does have its particular beneficial effects on the restoration of the intestinal flora. The dried chicory root component however needs to be used during the whole critical period. In certain embodiments, the pea cell wall fiber can be withdrawn after a while, once the faeces seem solid. In such case the chicory root administration can be continued separately to restore the gut flora. In case of sudden reappearance of liquid faeces, pea cell wall fiber could be administered again.

Aspect 12. The composition for use according to any one of claims 1 to 11, wherein said composition is administered in an amount of between 0.1 to 2% by weight of the total daily dry matter feed of the animal or poultry for preventive treatment of said *Brachyspira* infection. In a preferred embodiment, of said aspect, the amount of composition is set at between 0.2 and 1.0% by weight such as between 0.2 and 0.5% by weight of the total daily dry matter feed.

Aspect 13. The composition for use according to any one of claims 1 to 11, wherein said composition is administered in an amount of between 1 to 10% by weight of the total dry matter feed of the animal or poultry for reducing or treating said *Brachyspira* infection. In a preferred embodiment, of said aspect, the amount of composition is set at between 1.0% by weight and 5.0% by weight such as between 1.5% by weight and 4.0% by weight of the total daily dry matter feed, such as between 2.0 and 4.0% by weight.

Aspect 14. A solid or liquid feed product or feed supplement comprising between 0.1 and 10% by weight, preferably between 3 and 9% by weight, 4 and 8% by weight or 5 and 7% by weight, most preferably between 2 and 4% by weight of the composition of any one of aspects 1 to 8.

Aspect 15. Use of a composition according to any one of aspects 1 to 8 for preparing a feed additive, or for the production of a solid or liquid feed product or feed supplement, preferably wherein said composition is added in an amount of 0.1 and 10% by weight, preferably between 3 and 9% by weight, 4 and 8% by weight or 5 and 7% by weight, most preferably between 2 and 4% by weight, or preferably between 0.1 and 5% by weight, such as between 0.1 and 2% by weight, such as between 0.2 and 1.0% by weight, such as between 0.2 and 0.5% by weight of said composition.

Aspect 16. Method of reduction, treatment and/or prevention of *Brachyspira* infection in an animal, human or in poultry comprising administering the composition according to any one of aspect 1 to 8, or a solid or liquid feed product or feed supplement comprising such.

Aspect 17. The method according to aspect 16, for reduction, treatment and/or prevention of any one or more of: swine dysentery, Porcine Intestinal Spirochetosis (PIS), Avian Intestinal Spirochetosis (AIS) in an animal or in poultry.

Aspect 18. The method according to aspect 16 or 17, wherein said *Brachyspira* infection is caused by any one or more of *B. murdochii B. innocens B. intermedia B. hyodysenteriae, B. pilosicoli, B. suanatina, B. hampsonii, B. canis* and *B. aalborgi*.

Aspect 19. A food or beverage product or food supplement comprising a composition as defined in any one of aspects 1 to 8.

Aspect 20. Method of reduction, treatment and/or prevention of *Brachyspira* infection in human, comprising the administration of a therapeutically effective amount of the composition according to any one of aspects 1 to 8, or by administering a food product, beverage product or food supplement comprising such a composition.

Aspect 21. The method according to aspect 20, for reduction, treatment and/or prevention of Human Intestinal Spirochetosis (HIS) in human.

Aspect 22. The method according to aspect 20 or 21, wherein said *Brachyspira* infection is caused by *B. pilosicoli* or *B. aalborgi*.

DETAILED DESCRIPTION OF THE INVENTION

Before the present invention is described, it is to be understood that this invention is not limited to particular compositions, compounds, methods, components, or combinations thereof, or methods and uses of such compositions or compounds described, as such compositions, compounds or methods, and combinations thereof, or methods and uses of such compositions or compounds, may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of", as well as the terms "consisting essentially of", "consists essentially" and "consists essentially of".

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−20% or less, preferably +/−10% or less, more preferably +/−5% or less, and still more preferably +/−1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any or ≥7 etc. of said members, and up to all said members.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment but may. Furthermore, the particular features, structures or characteristics may be combined in any suitable manner, as would be apparent to a person skilled in the art from this disclosure, in one or more embodiments. Furthermore, while some embodiments described herein include some, but not other features included in other embodiments, combinations of features of different embodiments are meant to be within the scope of the invention, and form different embodiments, as would be understood by those in the art. For example, in the appended claims, any of the claimed embodiments can be used in any combination.

The following detailed description, therefore, is not to be taken in a limiting sense, and the scope of the present invention is defined by the appended claims.

As used herein, the terms "degree of polymerization" or "(DP)" relates to the number of monosaccharide residues present in an oligo- or polysaccharide. Often also the parameter average degree of polymerization is used. The degree of polymerization is a measure of molecular weight (MW). The DP can be calculated as the ratio of the total MW of the polymer or oligomer and the MW of the repeating units.

As used herein, the term "inulin" refers to a mixture of oligo- and/or polysaccharides of fructose which may have a terminal glucose. Inulins belong to a class of fibers known as fructans. In an embodiment, Inulin can be represented, depending from the terminal carbohydrate unit, by the general formulae GFn and Fm, wherein G represents a glucose unit, F represents a fructose unit, n is an integer representing the number of fructose units linked to the terminal glucose unit, and m is an integer representing the number of fructose units linked to each other in the carbohydrate chain. Inulins for use in the present invention encompasses inulins with a terminal glucose which are also referred as alpha-D-glucopyranosyl-[beta-D-fructofuranosyl](n-1)-D-fructofuranosides, as well as inulins without glucose which are also referred as beta-D-fructopyranosyl-[D-fructofuranosyl](n-1)-D-fructofuranosides. Inulins for use in the present invention can also encompass the hydrolysis products of inulins such as oligofructoses, which are fructose oligomers with a degree of polymerization (DP) of 20, and they can also encompass fructose oligomers ending with a terminal glucose with a DP of 3-5 synthesized from saccharose. Suitable oligosaccharide chains of inulin from plant origin for use in the invention can have a degree of polymerization (DP) ranging from 3 to about 100. Inulin can be a liquid or a powder product.

As used herein, the terms "degree of polymerization" or "(DP)" relates to the number of monosaccharide residues present in an oligo- or polysaccharide. Often also the parameter average degree of polymerization is used. The average degree of polymerization (av DP) of a (polydispersed) oligo- or polysaccharide mixture is the mean of the degree of polymerization (DP) of all the molecules present in this saccharide mixture.

The degree of polymerization is a measure of molecular weight (MW). The DP can be calculated as the ratio of the total MW of the polymer or oligomer and the MW of the repeating units. In a particular embodiment, the inulin for use in the present composition has, an average degree of polymerisation (DP) by number below 50, for example between 2 and 50, for example between 2 and 40, for example between 2 and 30, for example between 5 and 30, for example between 5 and 20, for example between 5 and 15, and for example about 10.

As used herein, the term "synergism" or "synergy" refers to two or more agents working together to produce a result not obtainable by any of the agents independently. This term is used to describe a situation where different entities cooperate advantageously for a final outcome. As used herein the terms "synergistic amounts" or "synergetic amounts" refer to amounts of dried chicory root and pea cell wall fibers which interact together such that the total effect is greater than the sum of the individual effects. Alternatively, the terms synergistic amounts" or "synergetic amounts" refer to amounts of inulin, sesquiterpene lactones and pea cell wall fiber which interact together such that the total effect is greater than the sum of the individual effects As used herein, the expression "%" refers to "% by weight (wt. %) expressed on dry matter". The % can be calculated on the total composition according to the present invention. Alternatively, the % can be calculated on the total food, beverage, food or feed supplement according to the present invention. Alternatively, the % can be calculated from the ratio between two or more compounds present in the composition. Alternatively, the % can be calculated from the ratio between two or more compounds, or between a compound and a composition, or between two or more compounds and one or more compositions according to the present invention.

The present invention relates to a composition comprising dried chicory root and pea cell wall fiber and its use for reducing, treating or preventing of Brachyspira infection. As used herein, the term "comprising" means that the composition contains at least dried chicory root and pea cell wall fibers. Alternatively, the term "comprising" means at least inulin and sesquiterpene lactones and pea cell wall fiber. Additional compounds, ingredients, products may or may not be present in such composition. Non-limiting examples of additional ingredients include other fermentable fibers, soluble and insoluble fibre components, carbohydrates, proteins, fats, minerals, vitamins.

In preferred embodiments the pea cell wall fiber is obtained from green pea or yellow pea, preferably obtained from yellow pea. Such fiber typically is pea fibre from dehulled peas (pea inner cell-wall fibers), or pea fiber present in the outer hull (pea outer-cell wall fibers), more preferably of yellow pea or green pea.

In an embodiment, the composition comprising dried chicory root and pea cell wall fiber is used for the preparation of a feed or a medicament for reducing, treating or preventing of Brachyspira infection. The present invention thus also concerns a method for preventing and/or treatment of Brachyspira infection comprising the administration of a physiologically or therapeutically effective amount of a composition comprising, consisting, or consisting essentially of dried chicory root and pea cell wall fiber in an animal or individual in need thereof.

As used herein the term "therapeutically effective amount" of said above-described composition relates to the amount or quantity of said composition required to achieve the desired therapeutic and/or prophylactic effect. Effective amounts may be measured and expressed in % of the composition on (daily) dry matter. Alternatively, effective amounts may be measured and expressed in g/day. A dosage twice a day can be preferred.

As used herein the term "physiologically effective amount" of said above-described composition relates to the amount or quantity of said composition required to achieve the desired physiological effect. Effective amounts may be measured and expressed in % of the composition on (daily) dry matter intake. Alternatively, effective amounts may be measured and expressed in g/day.

In an embodiment the Brachyspira infection to be reduced, treated or prevented is chosen from swine dysentery, Porcine Intestinal Spirochetosis (PIS), Avian Intestinal Spirochetosis (AIS), and Human Intestinal Sprirochetosis (HIS).

In a further embodiment, the Brachyspira infection is caused by any one or more of B. hyodysenteriae, B. pilosicoli, B. intermedia, B. canis and B. aalborgi. B. murdochii, and B. innocens.

The inventors surprisingly found that a combination of dried chicory root and pea cell wall fiber, and more specific a combination of inulin, sesquiterpene lactones and such pea cell wall fiber have synergistic effects on the control of Brachyspira infection, especially by reducing the number of Brachyspira in the faeces of sensible or infected animals. In a particular embodiment, the present invention provides a composition comprising dried chicory root and pea cell wall fiber, and more specific a composition comprising inulin, sesquiterpene lactones and pea protein wherein said dried chicory root and pea cell wall fiber are present in synergistic amounts. The compositions therefore offer great potential to better control the Brachyspira infection, for instance during the rearing of animals, for instance during the rearing of piglets or relocated retarded piglets as demonstrated in the examples. To animals that are subject to stress situations as preventive measure and eventually at a lower level.

Disclosed herein is a composition comprising dried chicory root, produced by a 2-step process of drying the raw chicory root and processing it in flakes of roughly 5 cm to 15 mm, preferably 3 cm to 15 mm, such as between 2 cm and 15 mm, re-drying said flakes and optionally grinding into small particles of approximately 0.1 to 2 mm, preferably between 0.5 to 1.5 mm, preferably of about 1 mm. The final dried chicory root product has a dry matter content of 88% by weight or more, preferably of 89% by weight or more, more preferably of 90% by weight or more, corresponding to a moisture content of between about 8 and 12% by weight, preferably of between 9 and 11% by weight. The composition disclosed herein is a natural composition, which has substantially not been treated chemically. Said dried chicory root composition comprises inulin, sesquiterpene lactone and chicory root pulp fraction.

The term "chicory root" as used herein refers to the root of chicory, in a preferred example, the species of chicory is Cichorium intybus L species. Chicory root comprises two main components, inulin and pulp. The raw chicory root comprises about 20-25% by weight of dry matter, which contains between 16-17% by weight inulin. When dried up to a dry matter content of around 90% by weight, this results in an inulin concentration in the dried chicory root composition of above 60% by weight, typically of about 65% by weight. Said inulin has an average degree of polymerization by number of at least 3. Additional components of the chicory root composition are sesquiterpene lactones such as the ones selected from: lactucine, dihydrolactucine, lactucopicrine and dihydrolactucopicrine. Typically, sesquiterpene lactones are present in dried chicory root in a concentration of around 0.4% by weight. The pulp fraction comprises soluble and insoluble fibers and cellulose.

Also the leaves of the chicory plant can be interesting, since they also contain about 0.25% by weight on dry matter of sesquiterpen lactones. The leaves could be directly fed to grazing cattle such as cows, sheep, goats, horses, camelids etc.

Dried chicory roots comprise inulin, sesquiterpenes lactone and a pulp fraction.

In an embodiment, inulin for use in the composition can originate from or be isolated or obtained from any natural source of inulin known to date, or can be enzymatically synthesized from saccharose, or can be a commercially available inulin. In an embodiment, inulin originates from or is isolated from elecampane, dandelion, dahlia, wild yarn, artichoke, Jerusalem artichokes, endive (witlof), chicory, jicama, burdock, onion, garlic, agave, yacón, banana, leek, asparagus or camas. In an embodiment, inulin is a (largely) linear fiber. Preferably, inulin originates from, or is isolated from chicory or Jerusalem artichokes. Suitable commercial inulin for use in the invention can be dried chicory root powder or flakes such as FIBROFOS™ 60.

FIBROFOS™ 60 (from Cosucra) contains 99.5% by weight dried chicory roots reduced to powder. FIBROFOS™ has a high inulin content (65% by weight on dry matter). This prebiotic inulin improves the bacterial flora by serving as an ideal substrate for the lactobacilli. FIBROFOS™ 60 provides monogastrics with a large quantity of soluble fibres and contributes to the health of the animal. In addition, it is rich in sesquiterpene lactones (±0.4% by weight). Those lactones are stimulating stomach and intestinal juice secretion (and consequently improving feed conversion) and it is particularly efficient as a de-wormer.

In a preferred embodiment, inulin for use in the composition originates from chicory and has an average DP of at least 3, preferably between 6 and 25.

In an embodiment, the composition for use in reducing, treating or preventing dysentery comprises at least 40 wt. % of inulin, preferably more than 60% by weight of inulin.

As used herein, the term "sesquiterpene lactones" refers to a class of chemical compounds, called sesquiterpenoids (built from three isoprene units) and contain a lactone ring. Sesquiterpene lactones are comprising at least artemisinin, lactucin, desoxylactucin, lactucopicrin, lactucin-15-oxalate, lactucopicrin-15-oxalate.

The present invention thus also relates to a composition comprising inulin, sesquiterpenoids and pea cell wall fibers wherein the sesquiterpenoids are chosen from lactucin, dihydrolactucin, lactucopicrin and dihydrolactucopicrin.

As used herein, the term "pulp fraction" refers to the pulp fraction comprised in the chicory root. It is mainly composing of soluble and insoluble fibres with a high water-retention capacity.

In a preferred embodiment, fiber for use in the composition originates from peas. Pea crops are very common in Northern Europe. Pea is an annual legume, with rapid growth. Yellow peas (*Pisum sativum*) are known since centuries as a healthy vegetable food and have been part of the human balanced diet thanks to the absence of lipids and their high protein, starch and fibre content. The main difference between green peas and yellow peas is the harvesting date: green peas are harvested before maturity; yellow peas are harvested at maturity. None of them are obtained by chemical or physical mutation. Pea ingredients are made from carefully selected peas. The separation technique of the pea components (proteins, fibres and starch) is based on an aqueous separation process without the use of organic solvents. A suitable pea fibre composition is the inner fibre of yellow peas, which comprises about 50% by weight fibres (from which about 40% by weight Pectin, about 45% by weight hemicellulose and about 15% by weight cellulose) and about 48% by weight of starch (from which about 15 to 20% by weight is resistant starch). An exemplary commercial product is for instance SWELITE™ or EXAFINE™ from Cosucra Groupe Warcoing. The pea cell wall fibers are mainly used to reduce wet faeces formation due to its high retention capacity (10:1 for water, 2.9:1 for oil), allowing the prolonged absorption of other nutritional or active ingredients. The pea cell wall fiber as such can also contribute to restoring of the gut flora (resistant starch effect).

The dried chicory root component has also some transit regulation effect (35% by weight pulp fraction) but will mainly intervene to restore the gut flora, due to its inulin and sesquiterpene lactone effect content. An exemplary commercial dried chicory root product is e.g. FIBROFOS™ 60 (Cosucra Groupe Warcoing).

The inner pea dietary fibres are typically composed of cellulose (±15% by weight), pectin (±40% by weight) and hemicellulose (±45% by weight).

In an embodiment, the composition of the present invention comprises dried chicory root (e.g. FIBROFOS™ 60—Cosucra Groupe Warcoing), or its cumulative respective components, and pea cell wall fiber (e.g. SWELITE™ pea inner cell wall fiber; or EXAFINE™ pea outer cell wall fiber—Cosucra Groupe Warcoing), or its cumulative respective components, in a weight ratio of 1/2 to 2/1, such as 1/1.5 to 1.5/1, such as preferably in a weight ratio of about 1/1. Exemplary weight ratios in percentages can be between 30-70% by weight of pea cell wall fiber and between 30-70% by weight dried chicory root component, such as between 40-60% by weight of pea cell wall fiber and 40-60% by weight of dried chicory root component, such as between 45-55% by weight of pea cell wall fiber and between 45-55% by weight of dried chicory root component, such as about 50% by weight of pea fiber and about 50% by weight of dried chicory root component. Said pea cell wall fiber and dried chicory root components can be administered simultaneously or said pea cell wall fiber component can be administered prior to administration of the dried chicory root composition. The inclusion of pea cell wall fiber is specifically intended to work as a carrier in order to stop the diarrheic liquid faeces on very short term. Once the faeces are under control, pea cell wall fiber could be withdrawn from the formula, although it does have its particular beneficial effects on the restoration of the intestinal flora. The dried chicory root component however needs to be used during the whole critical period.

Said dried chicory root component typically comprises at least 50% by weight of inulin, preferably at least 60% by weight of inulin, and/or comprises between 0.3 and 0.5% by weight such as about 0.4% by weight of sesquiterpene lactones, typically chosen from the group consisting of: lactucin, dihydrolactucin, lactucopicrin and dihydrolactucopicrin.

Said pea cell wall fiber component preferably is inner pea fibre, or pea fiber from dehulled peas, more preferably of yellow pea or green pea. Typically said pea cell wall fiber comprises about 50% by weight fibers and about 48% by weight starch, wherein the fiber component of said pea cell wall fiber comprises about 15% by weight cellulose, about 40% by weight pectin and about 45% by weight hemicellulose. Alternatively, said pea cell wall fiber is outer cell wall fiber, i.e. pea fiber present in the outer hull, more preferably of yellow pea or green pea. Typically said pea cell wall fiber comprises about 90% by weight fibers, wherein the fiber component of said pea cell wall fiber comprises about 50% by weight cellulose. In a specific embodiment, the composition of the present invention comprises the following components (based on a weight ratio of 1/1 of pea cell wall fiber and dried chicory root):

25 to 32.5% by weight of inulin,
0.15 and 0.25% by weight of sesquiterpene lactones,
about 25% by weight of pea cell wall fibers (said pea fibers preferably being composed of about 15% by weight cellulose, about 40% by weight pectin and about 45% by weight hemicellulose); and
about 24% by weight starch.

In a specific embodiment, the composition of the present invention comprises the following components (based on a weight ratio of 1/1 of pea outer cell wall fiber and dried chicory root):
- 25 to 32.5% by weight of inulin,
- 0.15 and 0.25% by weight of sesquiterpene lactones, and
- about 25% by weight of pea outer cell wall fibers (said pea fibers preferably being composed of about 50% by weight cellulose); Similar compositions can be calculated based on other weight ratios of the pea cell wall fiber and the dried chicory root components as indicated herein:

For a 1/2 weight ratio between dried chicory root and pea cell wall fiber, the following composition can be exemplified:
- 16.5 to 21.5% by weight of inulin,
- 0.1 and 0.2% by weight of sesquiterpene lactones,
- —about 33% by weight of pea cell wall fibers (said pea fibers preferably being composed of about 15% by weight cellulose, about 40% by weight pectin and about 45% by weight hemicellulose); and
- about 31.7% by weight starch.

For a 1/2 weight ratio between dried chicory root and pea outer cell wall fiber, the following composition can be exemplified:
- 16.5 to 21.5% by weight of inulin,
- 0.1 and 0.2% by weight of sesquiterpene lactones, and
- about 33% by weight of pea cell wall fibers (said pea fibers preferably being composed of about 50% by weight cellulose)

For a 2/1 weight ratio between dried chicory root and pea cell wall fiber, the following composition can be exemplified:
- 33 to 42.9% by weight of inulin,
- 0.2 and 0.33% by weight of sesquiterpene lactones,
- about 16.5% by weight of pea cell wall fibers (said pea fibers preferably being composed of about 15% by weight cellulose, about 40% by weight pectin and about 45% by weight hemicellulose); and
- about 15.9% by weight starch.

For a 2/1 weight ratio between dried chicory root and pea outer cell wall fiber, the following composition can be exemplified:
- 33 to 42.9% by weight of inulin,
- 0.2 and 0.33% by weight of sesquiterpene lactones, and
- about 16.5% by weight of pea cell wall fibers (said pea fibers preferably being composed of about 50% by weight cellulose)

Also the leaves of the chicory plant can be interesting, since they also contain about 0.25% by weight on dry matter of sesquiterpene lactones. The leaves could be directly fed to grazing cattle such as cows, sheep, goats, horses, camelids etc.

Determination of the molecular mass distribution of the fructan sample is done by High Performance Anion Exchange Chromatography coupled with Pulse Amperometric Detection (HPAEC-PAD) on a Thermo scientific—Dionex ICS 5000 chromatographic system. Separation of the various chain lengths is achieved by a Carbopac PA100 4 mm*250 mm (+ guard) at 40° C. with a flow rate of 1 ml/min. Sodium hydroxide 160 mM is used as eluent. A gradient of sodium acetate during the run allows to separate the various chain lengths. Fructan mixture standards at different concentrations are injected in order to draw the calibration curves and to assign the peaks in the chromatogram based on the retention time of the standard. The calibration curves allow determining the concentration of each molecular species in the sample.

From the obtained concentration distribution, the average polymerization degree in number $\overline{Dp_n}$ is calculated as:

$$\overline{Dp_n} = \frac{\sum_i N_i Dp_i}{\sum_i N_i}$$

Where Ni is the number of molecules having i residue and Dpi the number of residue. In an embodiment, the fructan as described herein, preferably inulin, has an average DP by number of at least 3. In an embodiment, the fructan as described herein, preferably inulin, has an average DP by number of at most 500. In an embodiment, said fructan, preferably inulin, has an average DP by number of at least 3, for example of at least 5, for example of at least 7, for example of at least 10, for example at least 15, for example at least 20, for example at least 25, for example at least 70. In an embodiment, the fructan as described herein, preferably inulin, has an average DP by number of at least 3 and of at most 500, preferably of at least 3 and at most 100, more preferably of at least 3 and of at most 30. In a further preferred embodiment, the fructan as described herein, preferably inulin, comprises or consists of fructooligosaccharides (FOS). In a further preferred embodiment, the fructan as described herein has an average DP by number of at least 3 and at most 20, preferably of at least 3 and at most 15, such as of at least 3 and at most 10. In yet another preferred embodiment, the fructan as described herein, preferably inulin, comprises or consists of hydrolyzed or partially hydrolyzed fructan, preferably inulin. Hydrolyzed fructan, such as hydrolyzed inulin, may for instance be obtained enzymatically (e.g. by inulinases) or may alternatively be obtained by acid and/or thermal hydrolysis.

As used herein, the term "sesquiterpene lactones" refers to a class of chemical compounds, called sesquiterpenoids (built from three isoprene units) and contain a lactone ring. Sesquiterpene lactone are comprising at least artemisinin, Lactucin, desoxylactucin, lactucopicrin, lactucin-15-oxalate, lactucopicrin-15-oxalate.

As used herein, the term "pulp fraction" refers to the pulp fraction comprised in the chicory root. It is mainly composing of soluble and insoluble fibres with a high-water retention capacity.

For use in the present invention, the chicory root is dried and ground into flakes of between 1 and 10 mm or into a fine powder having a mean particle diameter of less than 2 mm, preferably of between 0.6 and 1.2 mm, preferably of between 0.8 and 1 mm, between 0.1 to 2 mm, between about 0.5 to 1.5 mm, more preferably of about 1 mm. The mean particle size can be measured by any known technique such as sieving with a mesh having known sizes of openings and typically will be represented by any one of D10 (=arithmetic or number mean), D32 (=volume/surface mean (also called the Sauter mean)), or D43 (=the mean diameter over volume (also called the DeBroukere mean)).

Alternatively, raw inulin can be used, i.e. the raw juices of inulin obtained after extraction of the chicory pulp. This is prepared as follows: Inulin in raw form emerges from the diffusion after separation of the pulp. Inulin in raw form is practically composed of +/−75% inulin, +/−10% reducing sugars, protein residues (3%) minerals and sesquiterpene lactones, etc. The concentration of sesquiterpene lactones may therefore be somewhat higher than for the dried chicory root composition of the invention, and therefore contains +/−0.6% sesquiterpene lactones. However, this raw inulin has sticky and hygroscopic properties and is therefore not very easy in mixing and storage.

As a further alternative, a concentrate of sesquiterpene lactones can be used, resulting from separation of the minerals and sesquiterpene lactones from the raw inulin. This is prepared as follows: After obtaining the crude inulin, it is also possible to remove the raw juice from the inulin and to obtain a substance with a considerably higher concentration of sesquiterpene lactones. This concentrate could be in the form of a liquid syrup and would be particularly interesting as an ingredient for lick buckets (in the form of blocks of minerals with anti-fly/anti-mosquito and deworming effect.

As yet a further alternative, chicory seeds can be added in pastures, leading to feeding of cattle etc. of leaves and grass in the pasture.

Further disclosed is a method of producing a composition comprising dried chicory root comprising the following steps:
 a) washing of the raw chicory root material with water;
 b) cutting the raw material into flakes of about 1-15 mm with any suitable means, such as slicer; and
 c) drying the fresh chicory root flakes by direct or indirect heating by any suitable means, such as by means of heated air. It is preferred to keep the temperature of the drying process below 80° C., in order to avoid breakdown of the product. For example, the heating can be performed at a temperature of between 50 and 80° C., preferably between 60 and 70° C. Said drying step is typically done for at least 30 minutes, such as about 1 or 1.5 hours.

Said flakes can additionally be processed into a powder by:
 d) grinding, crushing or milling the dried flakes obtained in step c) into a fine powder having an average particle diameter of less than 2 mm, preferably of between 0.6 and 1.2 mm, more preferably between 0.8 and 1 mm, between 0.1 to 2 mm, between about 0.5 to 1.5 mm, more preferably of about 1 mm; and
 e) additional drying the milled dried chicory root obtained in step d); and
 f) optionally adding a silicate or calcium stearate to avoid water absorption.

Said milling, grinding or crushing can be performed by any suitable means in the art such as rotor mill, ball mill, cutter mill, hammer mill or other mills and grinders or crushers known in the art.

Alternatively, the chicory root material can be dried by direct heating, wherein the temperature is at least of 100° C., such as for example 120° C. for at least 1 second, such as for example for about 0.5 or 1 minute, or more, such as for example for up to 15 minutes.

The pee cell wall fiber as defined herein can be produced using a wet process to separate the fiber and starch particles from the protein of the pea. The hot wet process is solubilizing the protein components (also possible anti-nutritional factors as lectins and trypsin inhibitors) from the fiber parts. An exemplary method can be derived from WO2016/180888 from the same applicant. In short, said method is as follows:
 (a) Bring dehulled peas into contact with an aqueous phase in order to from an aqueous solution comprising pea;
 (b) leave said peas in the aqueous composition to hydrate for at least 30 minutes and at most 15 hours;
 (c) grind said peas thereby obtaining ground peas;
 (d) fractionate said ground peas in order to obtain at least an extract of peas comprising pea cell wall fibers.

Said fibers are then purified from said composition, which comprises at least one separation step selected from decanting, centrifugation and/or filtration. Typically said fractionation step is performed at a pH of at least 6.

Optionally, said composition comprising pea cell wall fibers can be subjected to a fermentation step.

Said pea inner cell wall fiber component typically comprises:
 a ratio fibers/starch of at least 30/70 and at most 85/15, more preferably a ratio fibers/starch of at least 40/60 and at most 70/30; and/or
 a quantity of fibers of at least 35% and at most 80% by weight of dry matter as measured by the method AOAC-985.29, more preferably a quantity of fibers between 40% and 55% by weight of dry matter as measured by the method AOAC-985.29; and/or
 a dry matter content of at least 80% and at most 95% by weight based on the weight of total extract, preferably a dry matter content of between 86 and 94% by weight based on the weight of total extract, more preferably a dry matter content of between 88 and 92% by weight based on the weight of total extract; and/or
 a protein content of less than 5% by weight of dry matter; and/or
 having a water retention of at least 9 g water/g of dry matter and at most 19 g water/g dry matter; more preferably of between 9 and 17 g water/g of dry matter. A commercially available product representing pea inner cell wall fibers is SWELITE™ (COSUCRA Groupe Warcoing SA, Belgium).

Said pea outer (hull) cell wall fiber component typically comprises:
 a ratio fibers/starch of at least 15/1 and preferably at least 16/1, more preferably a ratio fibers/starch of at least 17/1 (85/5% by weight on total dry matter); and/or
 a quantity of fibers of at least 85% by weight and preferably about 90% by weight of dry matter as measured by the method AOAC-985.29, more preferably a quantity of fibers between 80 and 95% by weight of dry matter as measured by the method AOAC-985.29; and/or
 a dry matter content of at least 80% by weight and preferably about 90 to 95% by weight based on the weight of total extract, preferably a dry matter content of between 86 and 94% by weight based on the weight of total extract, more preferably a dry matter content of between 90 and 94% by weight based on the weight of total extract; and/or
 a protein content of equal to or less than 7% by weight of dry matter; and/or
 having a water retention capacity of about 2 to 5 g water/g of dry matter, such as 3 or 4 g water/g of dry matter.

A commercially available product representing pea outer cell wall fibers is EXAFINE™ (COSUCRA Groupe Warcoing SA, Belgium).

The composition according to the invention can be supplemented to the feed of an animal as a functional feed additive or a prebiotic, or to human food or beverage, for instance to functional food or beverage, dietetic food and/or food supplements, as a food additive or a prebiotic. The present invention also encompasses a method for preparing a feed or food product or beverage or feed or food supplement comprising the steps of: (a) providing a composition according to the present invention, and (b) formulating said composition into a feed product, a food product, a beverage or a supplement.

The present invention also concerns a feed product containing the composition according to the present invention, as well as a food product containing the same composition, a beverage containing the same and a food supplement containing the same.

The composition of the invention may be used as a feed additive or in the production of a feed or as a basis for a solid or liquid feed supplement. In an embodiment, the feed or feed supplement comprises between 2 and 10% by weight of the composition according to the present invention. In a preferred embodiment, the feed or feed supplement comprises between 4 and 8% by weight, or between 3 and 6% by weight of the composition according to the present invention. In an even more preferred embodiment, the feed or feed supplement comprises between 2 and 4% by weight of the composition according to the present invention.

The composition of the invention may be used as a food additive, or in the production of food or beverage, or as a basis for a food supplement. In an embodiment, the food or beverage or supplement comprises an amount suitable to result in a dosage of between 0.1 and 10 g per day of the composition according to the present invention.

Alternatively, said amount can be calculated on an amount per serving of said food or beverage or supplement.

In a preferred embodiment, the food or beverage or supplement comprises between 0.5 and 5 g of the composition according to the present invention per serving of said food or beverage or supplement. In an even more preferred embodiment, the food or beverage or supplement comprises between 1 and 4 g of the composition according to the present invention per serving of said food or beverage or supplement.

For human use, a dosage use of the composition would typically be in the range of between 5 and 15 g per day of inulin and a dosage of fiber of between 25-30 g per day. This corresponds roughly to a dosage of the composition as defined herein within the range of 5 to 60 g per day, such as of between 5 and 40 g per day such as between 5 and 20 g per day.

For pharmaceutical use, the compositions of the invention may be formulated as a pharmaceutical preparation comprising dried chicory root and pea cell wall fiber and at least one pharmaceutically acceptable carrier, diluent or excipient and/or adjuvant, and optionally one or more further pharmaceutically active compounds. Alternatively said pharmaceutical preparation comprises inulin, sesquiterpene lactones and pea fibres and at least one pharmaceutically acceptable carrier, diluent or excipient and/or adjuvant, and optionally one or more further pharmaceutically active compounds. Such a formulation may be in a form suitable for oral administration.

In an embodiment, the present composition can optionally be combined with at least one pharmaceutically acceptable carrier for oral administration. When combined with a carrier, the weight percent of the carrier on the total composition can be between 1 and 85% by weight. Typical carriers are food and water. If soluble fiber is used, the combination of an aqueous carrier and the fiber will be a solution. If insoluble fiber is used, the combination of an aqueous carrier and the fiber will be a suspension. The compositions can include an inert diluent or an edible carrier. They may be enclosed in gelatin capsules or compressed into tablets. For the purpose of oral therapeutic administration, the composition can be incorporated with excipients and used in the form of tablets, troches, suppositories or capsules. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents. The composition can be administered as a component of an elixir, suspension, syrup, wafer, chewing gum or the like. A syrup may contain, in addition to the active compounds, sucrose as a sweetening agent and certain preservatives, dyes and colorings and flavors. The composition can also be mixed with other active materials which do not impair the desired action, or with materials that supplement the desired action.

The pharmaceutical preparations are preferably in a unit dosage form, and may be suitably packaged, for example in a box, blister, vial, bottle, sachet, ampoule or in any other suitable single-dose or multi-dose holder or container (which may be properly labelled); optionally with one or more leaflets containing product information and/or instructions for use.

The present composition will generally be administered in an effective amount, which, upon suitable administration, is sufficient to achieve the desired physiological, therapeutic and/or prophylactic effect in the animal or individual to which it is administered. It is to be further understood that for any particular subject, specific dosage regimens should be adjusted over time according to the individual need and the professional judgment of the person administering or supervising the administration of the compositions, and that the dosage ranges set forth herein are exemplary only and are not intended to limit the scope or practice of the composition.

The invention will now be illustrated by means of the following examples, which do not limit the scope of the invention in any way.

EXAMPLES

1. Materials and Methods 1.1. Products

The inulin and sesquiterpane lactones source used in this trial was FIBROFOS™ 60 (COSUCRA Groupe Warcoing SA, Division SOCODE, Belgium), which is a chicory root composition dried at low temperature and reduced to a powder or flake (schredded) product. FIBROFOS™ 60 has a dry matter of 90% by weight and generally contains, on dry matter, about 65% by weight of inulin and about 0.4% by weight of sesquiterpene lactones. The remaining fraction (+/−35% by weight) is composed of mainly insoluble fibres (cellulose and hemicellulose) and soluble fibres (pectin).

The pea fibre source in this trial was SWELITE™ (COSUCRA Groupe Warcoing SA, Belgium), which is a fibre source with a dry matter of minimal 86% by weight and a composition on dry matter of about 48% by weight of total dietary fiber, about 36% by weight of starch and about 7% by weight of protein. The dietary fibres are composed on dry matter of cellulose (±15% by weight), pectin (±40% by weight) and hemicellulose (±45% by weight). Alternative pea fibre sources can be those obtained from the pea hull or outer cell wall, e.g. commercially available as EXAFINE™ (COSUCRA Groupe Warcoing SA, Belgium). EXAFINE™ is a fibre source with a dry matter of minimal 86% by weight and a composition on dry matter of minimal 85% by weight of total dietary fiber, maximum about 5% by weight of starch and maximum about 7% by weight of protein. The dietary fibres are composed of cellulose in an amount of about 50% by weight on dry matter.

1.2. Outline of Study

A holding with 6400 fattening pigs sourced from a single rearing unit experienced significant production losses due to diarrhoea, ill thrift, and weight loss attributed to *Lawsonia intracellularis* and pathogenic *Brachyspira* spp. The feed additives FIBROFOS™ 60 and SWELITE™, respectively comprising dried chicory root and pea cell wall fiber, were introduced to 348 of the lightest runners in the group and faecal samples were analysed using PCR and culture before and after the as well as shortly before slaughter. Results depicted a drop in the occurrence of both *Lawsonia intracellularis* and *Brachyspira* spp. in the experimental group. The trend of this case study suggests that the use of these feed additives may help reduce the use of antibiotics in practice.

On Jun. 22, 2018, 720 weaners arrived at the holding. The lightest weaners (n=348) were separated from the rest of the group and kept in two sections on the farm.

These were referred to as the experimental group. Two weeks later, faecal samples were taken at random from 29 piglets displaying diarrhoea, dehydration, or reduced weight gain. These 29 animals were marked and kept with the experimental group in a separate stall. Faecal swabs without medium were examined for *Lawsonia intracellularis* at the IVD laboratory in Hannover. They were pooled in sets of three. Faecal swabs with medium were individually cultured for *Brachyspira* spp. at the Microbiological Institute of the Veterinary School (TiHo) in Hannover. The results were classified as high (hgr), middle (mgr), or low (lgr) incidence of the bacteria in each sample.

Both feed additives (FIBROFOS™ 60 and SWELITE™) were used in the experimental group from Jul. 17, 2018 through Aug. 27, 2018 in an amount of 2% by weight on dry matter of both FIBROFOS™ 60 and SWELITE™ Thereafter, 23 animals were tested for the second time using faecal swabs once more. The third sampling occurred shortly before slaughter on May 3, 2018.

Time Line of Experiment:
Date of stock introduction (n=720): 22.06.2018
Use of Tylosin Tartrate: 26.06.2018-05.07.2018
1st faecal sampling: (n=29) 06.07.2018
Feeding of FIBROFOS™ 60 and SWELITE™ (both in amount of 2% by weight on dry matter (DM)): 17.07.2018-27.08.2018
2nd faecal sampling (n=23): 06.09.2018
3rd faecal sampling (n=23): 28.09.2018
Slaughter (day of fattening): 105th and 124th 2. Results Microbiological Results:

When the first faecal swabs were taken post-treatment, the detection rate for *Lawsonia intracellularis* and *Brachyspira* spp. was 90% of pool samples and 83% of individual samples, respectively (Table 1). The main *Brachyspira* type identified was *B. intermedia* (83%) (Table 2). In total, 69% of all samples were considered "high grade", and 83% of all positive samples were classified "high grade" (Table 3). At a second faecal sampling, two months post treatment with Tylosin Tartrate and two weeks post feeding additives FIBROFOS™ 60 and SWELITE™, the number of pigs that were tested was reduced to 23, due to death or euthanasia because of welfare reasons. *Lawsonia intracellularis* was found in 12.5% of pool samples. The number of *Brachyspira* spp. positive culture samples was reduced by more than half at 39% compared to the first sampling. While the most common *Brachyspira* type was still *B. intermedia* (66.7%) (Table 2), there was only one high grade sample in total (Table 3). When taking the third faecal swabs—just before first slaughter—neither *Lawsonia intracellularis* nor *Brachyspira intermedia*, *B. innocens*, or *B. murdochii* (i.e. pathogenic *Brachyspira* species) could be detected anymore (Table 1, Table 2). However, 91% of samples were positive for other *Brachyspira* spp. (Table 1), of which 48% were considered "high grade" (Table 3).

TABLE 1

Positive results for *Lawsonia intracellularis* and various *Brachyspira* spp. at first, second, and third sampling of the fattening pigs

|  | $1^{st}$ Sampling N = 29 (10 pools) | $2^{nd}$ Sampling N = 23 (8 pools) | $3^{rd}$ Sampling N = 23 (8 pools) |
|---|---|---|---|
| *Lawsonia intracellularis* | 9/10 (90%) | 1/8 (12.5%) | 0/8 (0%) |
| *Brachyspira* spp. (total) | 24/29 (83%) | 9/23 (39%) | 21/23 (91%) |

TABLE 2

Breakdown and grading of the detected *Brachyspira* species at first, second, and third faecal sampling of the fattening pigs.

|  | 1st. sampling (29 samples, 10 Pools) | 2nd. sampling (23 samples, 8 Pools) | 3rd. sampling (23 samples, 8 Pools) |
|---|---|---|---|
| *Lawsonia intracellularis* | 9/10 Pools positive (90%) | 1/8 Pools positive (12.5%) | 0/8 Pools positive (0%) |
| *Brachyspira intermedia* | 19 hgr., 1 lgr. | 1 hgr., 2 mgr., 3 lgr. | none |
| *Brachyspira murdochii* | none | 1 lgr. | none |
| *Brachyspira innocens* | 2 lgr. | 1 lgr. | none |
| *Brachyspira*, other* | 1 hgr., 1 lgr. | 1 lgr. | 10 hgr., 3 mgr., 8 lgr. |
| *Brachyspira* spp. | 24/29 samples positive (83%) | 9/23 samples positive (39%) | 21/23 samples positive (91%) | lgr. Low grade infection;
mgr. medium grade infection;
hgr. High grade infection
"*Brachyspira*, other" includes other *Brachyspira* spp. not listed in the table above. However, pathogenic *B. hyodysenteriae*, *B. pilosicoli*, *B. hampsonii* could be ruled out and are therefore not included in "other"It is obvious that there has been a shift in *Brachyspira* spp.

TABLE 3

The grading of positive samples in relation to the total number of samples and the total of all positive samples at first, second, and third fecal sampling of all fatteners.

|  | 1st sampling N = 29 | 2nd sampling N = 23 | 3rd sampling N = 23 |
|---|---|---|---|
| Positive samples | 24/29 (83%) | 9/23 (39%) | 21/23 (91%) |
| High grade positive samples/all samples | 20/29 (69%) | 1/23 (5%) | 10/23 (43%) |
| High grade positive samples/all positives | 20/24 (83%) | 1/9 (11%) | 10/21 (48%) |

Production Performance

Table 4 below depicts the production data of the control compared to the experimental group. While the average weight of the weaners at introduction to the unit was 29 kg in the control group, it was less than 24 kg in the experimental group. On average, the investigated set took longer (105 vs. 85 fattening days) until they reached the slaughter weight despite the daily weight gain of both groups being very similar (969 and 998 gigajoule per day).

TABLE 4

Production Performance

| Production Parameters | Control Group * | Experimental Group |
|---|---|---|
| Stock Introduction weight (kg) | 29 | <24 |
| Fattening days until slaughter | 85 | 105 |
| Fattening days (total) | 120 | 124 |
| Daily Weight Gain until day 60 (g/day) | 969 | 998 |

* Control group data taken from performance averages of this particular holding

3. Conclusion

In conclusion, despite the small sample size and biased experimental group assignment, a trend is shown that feed additives containing inulin and hydrophilic plant-based pea inner or outer cell wall fibres can act as a means of disease control and improve production data. Considering the increasing risk of antimicrobial resistance, it is important to find other ways to support the immunity of animals.

The invention claimed is:

1. A method for treating infections with pathogenic *Brachyspira* ssp. in animals and poultry, comprising administering a composition comprising dried chicory root and pea cell wall fibers, wherein the weight ratio of said dried chicory root to said pea cell wall fiber is between 1/2 and 2/1, wherein said composition is administered in an amount of between 0.1 to 10% by weight of the total dry matter feed of the animal or poultry in need thereof.

2. The method according to claim 1, wherein said dried chicory root comprises inulin, sesquiterpene lactones, a soluble fraction and an insoluble fraction.

3. The method according to claim 1, wherein said dried chicory root comprises at least 50% by weight of inulin, and/or comprises between 0.3 and 0.5% by weight of sesquiterpene lactones.

4. The method according to claim 1, wherein said dried chicory root comprises sesquiterpene lactones chosen from the group consisting of: lactucin, dihydrolactucin, lactucopicrin and dihydrolactucopicrin.

5. The method according to claim 1, wherein said pea cell wall fiber is pea inner cell wall fibers or pea fiber present in the outer hull.

6. The method according to claim 5, wherein said pea inner cell wall fiber comprises about 50% by weight fibers and about 48% by weight starch on total dry matter content.

7. The method according to claim 5, wherein said pea outer cell wall fiber comprises at least about 85% by weight fibers on total dry matter content.

8. The method according to claim 1, wherein the fiber component of said pea cell wall fiber comprises about 15% by weight cellulose, about 40% by weight pectin and about 45% by weight hemicellulose.

9. The method according to claim 1, wherein said pathogenic *Brachyspira* infection is resulting in a disorder selected from: swine dysentery, Porcine Intestinal Spirochetosis (PIS), and Avian Intestinal Spirochetosis (AIS).

10. The method according to claim 1, wherein said pathogenic *Brachyspira* infection is caused by any one or more of: *B. murdochii B. innocens B. intermedia B. hyodysenteriae, B. pilosicoli, B. suanatina, B. hampsonii, B. canis* and *B. aalborgi*.

11. The method according to claim 1, wherein said pea cell wall fiber and dried chicory root components are administered simultaneously or wherein said pea cell wall fiber component is administered prior to administration of the dried chicory root composition.

12. The method according to claim 1, wherein said composition is administered in an amount of between 1 to 10% by weight of the total dry matter feed of the animal or poultry for treating said *Brachyspira* infection.

13. The method according to claim 1, wherein the weight ratio of said dried chicory root to said pea cell wall fiber is between 1/1.5 and 1.5/1.

14. The method according to claim 1, wherein the weight ratio of said dried chicory root to said pea cell wall fiber is about 1/1.

15. The method according to claim 2, wherein said insoluble fraction comprises pulp and/or the soluble fraction comprises pectin.

16. The method according to claim 1, wherein said pea cell wall fiber is pea inner cell wall fiber or pea fiber present in the outer hull of yellow pea or green pea.

* * * * *